(12) United States Patent
Jongen

(10) Patent No.: US 9,451,688 B2
(45) Date of Patent: Sep. 20, 2016

(54) DEVICE AND METHOD FOR PARTICLE BEAM PRODUCTION

(75) Inventor: Yves Jongen, Louvain-la-Neuve (BE)

(73) Assignee: Ion Beam Applications S.A., Louvain-La-Neuve (BE)

( * ) Notice: Subject to any disclaimer, the term of this patent is extended or adjusted under 35 U.S.C. 154(b) by 182 days.

(21) Appl. No.: 13/380,446

(22) PCT Filed: Jun. 24, 2010

(86) PCT No.: PCT/EP2010/059001
§ 371 (c)(1),
(2), (4) Date: Mar. 13, 2012

(87) PCT Pub. No.: WO2010/149740
PCT Pub. Date: Dec. 29, 2010

(65) Prior Publication Data
US 2012/0160996 A1    Jun. 28, 2012

(30) Foreign Application Priority Data
Jun. 24, 2009   (EP) .................... 09163686

(51) Int. Cl.
*H05H 7/08*     (2006.01)
*H05H 7/00*     (2006.01)
*A61N 5/10*     (2006.01)

(52) U.S. Cl.
CPC .............. *H05H 7/00* (2013.01); *A61N 5/1048* (2013.01); *A61N 5/1067* (2013.01); *A61N 2005/1087* (2013.01)

(58) Field of Classification Search
CPC ........... A61N 5/10; H05H 7/08; H05H 13/02
USPC .......... 315/503, 500, 502; 250/252.1, 492.3, 250/492.1, 493.1, 423 R, 398; 313/62
See application file for complete search history.

(56) References Cited

U.S. PATENT DOCUMENTS 6,873,123 B2 *   3/2005   Marchand et al. ........... 315/502
7,456,415 B2 *   11/2008  Yanagisawa et al. ..... 250/492.3
(Continued)

FOREIGN PATENT DOCUMENTS

EP    1 265 462 A1    12/2002
EP    2 026 640 A2    2/2009
(Continued)

OTHER PUBLICATIONS

Amaldi, Cyclinacs: Novel Fast-Cycling Accelerators for Hadrontherapy, 2007, Cyclotrons and Their Applications, 18th International Conference, pp. 166-168.*
(Continued)

*Primary Examiner* — Don Le
(74) *Attorney, Agent, or Firm* — Fitch, Even, Tabin & Flannery LLP

(57) ABSTRACT

The present invention relates to a pulsed beam particle accelerator which can be used for particle radiation therapy. More particular, a device and method are provided to control the number of particles within a beam pulse. The particle accelerator comprises means for varying the number of particles within each beam pulse of said pulsed ion beam from a minimum value to a maximum value as function of the value of a beam control parameter. For each particle irradiation the required number of particles for each beam pulse is controlled by defining a value for said beam control parameter based on calibration data.

16 Claims, 3 Drawing Sheets

(56) References Cited

U.S. PATENT DOCUMENTS

| | | | | |
|---|---|---|---|---|
| 2007/0001128 A1* | 1/2007 | Sliski | ............... | H05H 13/02 250/492.3 |
| 2008/0093567 A1 | 4/2008 | Gall | | |
| 2008/0270517 A1* | 10/2008 | Baumann et al. | ............ | 709/202 |
| 2009/0236545 A1* | 9/2009 | Timmer | ............... | A61N 5/10 250/492.1 |
| 2009/0296885 A1* | 12/2009 | Boeh | ............... | A61N 5/1042 378/65 |
| 2009/0309046 A1* | 12/2009 | Balakin | ............ | A61N 5/1049 250/492.3 |

FOREIGN PATENT DOCUMENTS

| | | | |
|---|---|---|---|
| JP | 10247600 A | 9/1998 | |
| JP | 10270200 A | 10/1998 | |
| WO | 03/092340 A1 | 11/2003 | |
| WO | 2009/056165 A1 | 5/2009 | |

OTHER PUBLICATIONS

Grozinger, Volume Conformal Irradiation of Moving Target Volumnes with Scanned Ion Beams, 2004, pp. 1-90.*

Ugo Amaldi, "Cyclinacs: Novel Fast-Cycling Accelerators for Hadrontherapy." Proceedings of 18th International Conference on Cyclotrons and Their Applications: Catania, Italy; Oct. 1-5, 2007, 2008, pp. 166-168.

E. Pedroni et al., "A Novel Gantry for Proton Therapy At The Paul Scherrer Institute." AIP Conference Proceedings AIP USA, No. 600, 2001, pp. 13-17.

Uli Weber et al., "Depth Scanning for a Conformal Ion Beam Treatment of Deep Seated Tumours." Physics in Medicine and Biology IOP Publishing UK, vol. 45, No. 12, Dec. 2000, pp. 3627-3641.

Eros Pedroni et al., "The 200-MeV Proton Therapy Project At The Paul Scherrer Institute: Conceptual Design and Practical Realization." Medical Physics USA, vol. 22, No. 1, Jan. 1995, pp. 37-53.

Shinji Sato et al., "Dynamic Intensity Control System with RF-knockout Slow-Extraction in the HIMAC Synchrotron." Nuclear Instruments and Methods in Physics Research A 574, 2007, pp. 226-231.

European Search Report, European Patent Application No. 09 16 3686, date of completion of the search Nov. 30, 2009, 3 pages.

International Search Report and The Written Opinion, International Patent Application No. PCT/EP2010/059001, date of the actual completion of the search Oct. 14, 2010, 18 pages.

Notification of Transmittal of the International Preliminary Report on Patentability, International Patent Application No. PCT/EP2010/059001, date of the actual completion of the report Oct. 12, 2011, 9 pages.

* cited by examiner

DEVICE AND METHOD FOR PARTICLE BEAM PRODUCTION

CROSS REFERENCE TO RELATED APPLICATIONS

This application is a national phase application of International Application No. PCT/EP2010/059001, filed Jun. 24, 2010, designating the United States and claiming priority to European Patent Application No. 09163686.0, filed Jun. 24, 2009, which is incorporated by reference herein in its entirety.

FIELD OF THE INVENTION

The present invention relates to the field of pulsed beam accelerators for use in charged particle radiation therapy (e.g. proton, carbon ion). More particularly, this invention relates to the control of the amount of particles within the beam pulses extracted from the accelerator.

STATE OF THE ART

In order to accelerate charged particles to energies for use in charged particle radiation therapy (e.g. up to 250 MeV for proton therapy) many types of accelerators have been developed or proposed. Depending on the specific design of these accelerators some accelerators are producing a continuous particle beam (e.g. isochronous cyclotron) whereas other types of accelerators are producing a particle beam having a pulsed time structure (e.g. synchrocyclotron, fixed field alternating gradient accelerator, linear accelerator). Some basic components that these accelerators have in common is an ion source for producing the ionized particles to be accelerated and a radio frequency (RF) accelerator system intended to accelerate the ionized particles.

One of the first types of accelerators used for charged particle radiation therapy is a synchrocyclotron. The development of synchrocyclotrons is strongly linked with the development of proton therapy. At the Harvard university campus (Massachusetts, USA), a synchrocyclotron constructed in 1948 for use in physics research was upgraded for use in proton therapy and in 1961 first patients were treated using a 160 MeV proton beam the synchrocyclotron. Similar, at Orsay (France) a synchrocyclotron from 1954 was converted from particle research usage to proton therapy usage. First patient treatments at Orsay were started in 1991. More recently the development of a compact superconducting synchrocyclotron mounted on a gantry structure to allow rotation around a patient was announced by K. Gall (U.S. 2008/0093567).

In the field of charged particle radiation therapy besides a synchrocyclotron, another type of cyclotron namely an isochronous cyclotron is presently in use as well. The RF accelerator systems of both accelerators are different: an isochronous cyclotron is using a constant RF frequency while a synchrocyclotron is using a modulated RF frequency (typically modulated at a frequency between 200 and 1000 Hz). Indeed in a synchrocyclotron charged particles are extracted from the ion source and accelerated in discrete bunches to their final energy before a new total acceleration cycle is repeated. The frequency of this total acceleration cycle, i.e. the frequency at which beam pulses are generated and extracted from the accelerator corresponds to the modulation frequency of the RF (i.e. RF repetition rate). As a result the beam extracted from a synchrocyclotron is pulsed at the modulation frequency while the beam extracted from an isochronous cyclotron is continuous. The extracted beam from a synchrocyclotron will be delivered in beam pulses having a duration of e.g. 0.5 microseconds and beam pulses will be repeated typically every 2 milliseconds (=1/RF modulation frequency). Typical beam pulse durations can vary, and are typically lower than 50 ms.

In order to accommodate to the specific time structure of the synchrocyclotron beam, all current proton therapy facilities having a synchrocyclotron are limited to the use of the so-called double scattering technique for delivering charged particle radiation therapy. More advanced techniques for delivering charged particle radiation therapy such as the so-called scanning technique have not been used in combination with a synchrocyclotron due to problems resulting from the specific time structure of the extracted beam. For advanced scanning beam delivery techniques it is important to have a fast (microsecond level) and accurate (typically 1%) control of the extracted beam intensity.

The fact that a pulsed beam is a major disadvantage for use in particle therapy can be illustrated with an example of an advanced scanning beam delivery technique. An example of an advanced scanning beam delivery technique is the so called spot-scanning technique which is described by Pedroni et al. in Med. Phys., 1995, 22 (1), 37-53. With this technique the target volume is divided in a series of voxels (elementary target volume) and each voxel is then irradiated by performing a "spot" irradiation. Inbetween two spot irradiations the beam is interrupted. With a spot scanning system the dose to be delivered for each voxel is in general not the same and hence the number of particles to be delivered during each spot irradiation can be different for spot to spot. For each voxel a required dose specified by a treatment planning system needs to be delivered with high accuracy. A typical dose delivery accuracy required for each beam spot is 1%. One of the problems with a pulsed accelerator is that it is difficult to use such a beam time structure in combination with a spot scanning technique. Taking the example of a synchrocyclotron accelerator where the beam is delivered in pulses which are typically repeated every 2 milliseconds (=1/RF modulation frequency which typically lies between 200 and 1000 Hz) and where the pulse duration is typically 0.5 microseconds. Due to this small pulse duration it is impossible to stop the beam in the middle of a beam pulse and hence beam spot irradiations can only be delivered as an integer number of pulses. In order to obtain a dose delivery accuracy of 1% for each spot irradiation, it is necessary to deliver about 100 beam pulses for each spot irradiation. Knowing that a typical target volume is divided in about 5000 to 10000 voxels, the total irradiation time of the target volume is of the order of 1000 to 2000 seconds, which is an unacceptable long irradiation time. Moreover, Pedroni et al. proposed to perform multiple repainting of the target volume to compensate for organ motion and hence the total number of spot irradiations to complete a target irradiation is even more increased.

For other types of accelerators producing a pulsed beam, the same problem as described above will be encountered. Examples of other types of pulsed accelerators that have been proposed for use in charged particle radiation therapy are fixed field alternating gradient accelerators (FFAG's) and linear accelerators.

An example of a method and device for fast beam current regulation for use in advanced particle radiation therapy is described in U.S. Pat. No. 6,873,123 and WO2009056165 by the applicant. With this method and device the continuous current extracted from an isochronous cyclotron can be regulated with a precision of the order of 1 to 2%. In these beam regulation methods a feedback loop is used: the beam current of the proton beam is measured at the exit of the cyclotron and the measured beam current value is compared with the required value, the regulation loop adjusts for example a beam control parameter of the ion source in order to obtain a measured beam current equal to the required beam current. Similar, in WO2009056165 a control parameter of the RF acceleration system is adjusted to vary the extracted beam intensity. However, this method can not be applied to regulate the intensity of a single beam pulse extracted from a synchrocyclotron having the time structure as described above. Indeed, at the time the intensity of the beam pulse extracted from the synchrocyclotron is measured, the ion source is already shut off since a long time. Hence, it is impossible to use the measured intensity or number of particles within an extracted beam pulse and correct a control parameter of the ion source (or any other device that can vary the beam pulse intensity) to adjust the intensity of this same beam pulse that is already extracted from the accelerator.

Accordingly, no practical solution has been proposed so far to regulate the extracted beam from a pulsed accelerator on a pulse per pulse basis which may solve the above-mentioned drawbacks.

AIMS OF THE INVENTION

The present invention aims to provide a method and device which overcomes the problem of the prior art.

In particular the present invention aims to provide a method and device for controlling the number of particles within an extracted beam pulse of a pulsed accelerator.

SUMMARY OF THE INVENTION

The present invention is set forth and characterized by the appended claims.

According to a first aspect of the present invention, a particle accelerator of the type synchrocyclotron, linear accelerator or fixed field alternating gradient accelerator, for producing an energetic pulsed ion beam is provided. This accelerator comprises an ion source for producing ions and a radio frequency acceleration system for accelerating ions. The accelerator according to the invention further comprises:

Means for varying the number of particles within each beam pulse of said pulsed ion beam from a minimum value to a maximum value as function of the value of a beam control parameter, said parameter being related to the operation of the ion source and/or of the RF system;

A beam control device comprising:
an interface for receiving an external instruction specifying the required number of particles for each beam pulse;
means for storing a calibration table or storing parameter values of a mathematical function defining the relation between the value of said beam control parameter and said number of particles within a beam pulse;
means for determining the required value of said beam control parameter corresponding to said required number of particles using said calibration table or said mathematical function;
an interface for sending said required value of said beam control parameter to said means for varying;

In addition, according to the first aspect of the invention, the said beam control device further comprises:
an interface for receiving an external signal specifying the measured number of particles within a beam pulse, said measurement being performed with a beam monitor;
means for updating said calibration table or said parameter values in dependence of said measured number of particles.

In a preferred embodiment, the particle accelerator according to the invention further comprises:
control means for automatically generating said calibration table or said mathematical function by defining a number of different values for said beam control parameter, producing for each said value a beam pulse and measuring the corresponding number of particles within each produced beam pulse.

Advantageously, in a preferred embodiment, the particle accelerator further comprises:
control means for automatically readjusting said calibration table or said mathematical function after each beam pulse produced by said accelerator, said readjusting being made by comparing the said measured number of particles with the said required number of particles.

In one embodiment of the invention, the said means for varying the number of particles within each beam pulse comprises means for varying the arc current of said ion source.

In another embodiment of the invention, the said means for varying the number of particles within each beam pulse comprises means for varying the acceleration voltage of said radio frequency acceleration system.

Alternatively, in another embodiment of the invention, the said means for varying the number of particles within each beam pulse comprises means for varying the time period during which the said ion source is turned on.

According to a preferred embodiment of the invention, the said means for varying the number of particles within each beam pulse comprises means for varying the time difference between the moment the ion source is turned on and the moment the ions can start acceleration using said radio frequency acceleration system.

According to a first aspect of the invention, a particle radiotherapy system is provided comprising a particle accelerator having the characteristics of any of the above described embodiments of invention.

According to a preferred embodiment of the invention, the said particle radiotherapy system further comprises a spot scanning beam delivery device configured to provide a series of spot irradiations.

In one embodiment of the invention, the said spot scanning beam delivery device is configured to use a single beam pulse for each said spot irradiation.

In a preferred embodiment of the invention, the said spot scanning beam delivery device is configured to use two beam pulses to deliver the total required number of particles for each said spot irradiation, and said particle radiotherapy device is further comprising:
Means to define the required number of particles for the first of said two beam pulses as being a given percentage of the total required number of particles to be delivered for said spot irradiation;
Means to specify the required number of particles of the second of said two beam pulses as being the said total required number of particles for said spot irradiation minus the measured number of particles already delivered with said first beam pulse.

Alternatively, the said spot scanning beam delivery device is configured to use a variable number of beam pulses for each said spot irradiation, said particle radiotherapy device further comprising:

Means to define the required number of particles for all beam pulses of said variable number of beam pulses such that the sum of the required number of particles of all beam pulses except the last beam pulse equals a given percentage of the total number of particles to be delivered for said spot irradiation.

Means to specify the required number of particles for the last beam pulse of said variable number of beam pulses as being the total number of particles to be delivered for the said spot irradiation minus the measured number of particles already delivered for said spot irradiation.

According to a second aspect of the present invention, a method is provided for controlling the number of particles within a beam pulse from a pulsed beam particle beam accelerator of the type synchrocyclotron, linear accelerator or fixed field alternating gradient accelerator. These beam pulses can be used for performing particle beam irradiations. The said accelerator comprises means to vary the number of particles within each beam pulse as function of the value of a beam control parameter, said beam control parameter being related to the operation of the ion source and/or the RF system. The method of the invention comprises the steps of:

Generating calibration data comprising the sub-steps of:
1. Applying a value of said beam control parameter to said means for varying number of particles;
2. Producing and extracting a beam pulse from said accelerator;
3. Measuring number of particles within said extracted beam pulse;
4. Storing said measured number of particles within said extracted beam pulse;
5. Repeating steps 1 to 4 for a series of beam control parameter values;

Performing particle beam production comprising the sub-steps of:
1. Receiving an external instruction specifying for each beam pulse the required number of particles within a beam pulse;
2. Determining the required value of said beam control parameter corresponding to said required number of particles using said calibration data;
3. Applying said required value of beam control parameter to said means for varying number of particles;
4. Producing and extracting beam pulse from said accelerator.

Advantageously, in the method according to the invention for controlling the number of particles within a beam pulse, the step of performing particle beam production further comprising the additional sub-steps of:
5. Measuring the number of particles within said extracted beam pulse;
6. Making a comparison between said measured number of particles with said required number of particles;
7. Applying a correction to said calibration data based on said comparison;

The invention is also related to a method for performing a series of spot irradiations by a number of beam pulses with the system of the invention, characterized in that said method comprises for each spot of said series of spot irradiations the steps of:

defining the total required number of particles $T1$ to be delivered to said spot, specifying a total number of beam pulses for delivering said number of particles $T1$ and defining a required number of particles for each beam pulse of said total number of beam pulses, applying said beam pulses, except the last beam pulse, measuring the number of particles $A1$ of said beam pulses except the last beam pulse, before applying the last beam pulse, calculating the difference $T1-A1$ between the total required number of particles and the measured number of particles, specifying the required amount of particles in the last beam pulse $A2$ as equal to said difference $T1-A1$, applying the last beam pulse.

DETAILED DESCRIPTION OF PREFERRED EMBODIMENTS OF THE PRESENT INVENTION

The present invention will be now described in detail in relation to the appended drawings. However, it is evident that a person skilled in the art may conceive several equivalent embodiments or other ways of executing the present invention. The spirit and the scope of the present invention are therefore limited only by the terms of the claims.

Figure 1:
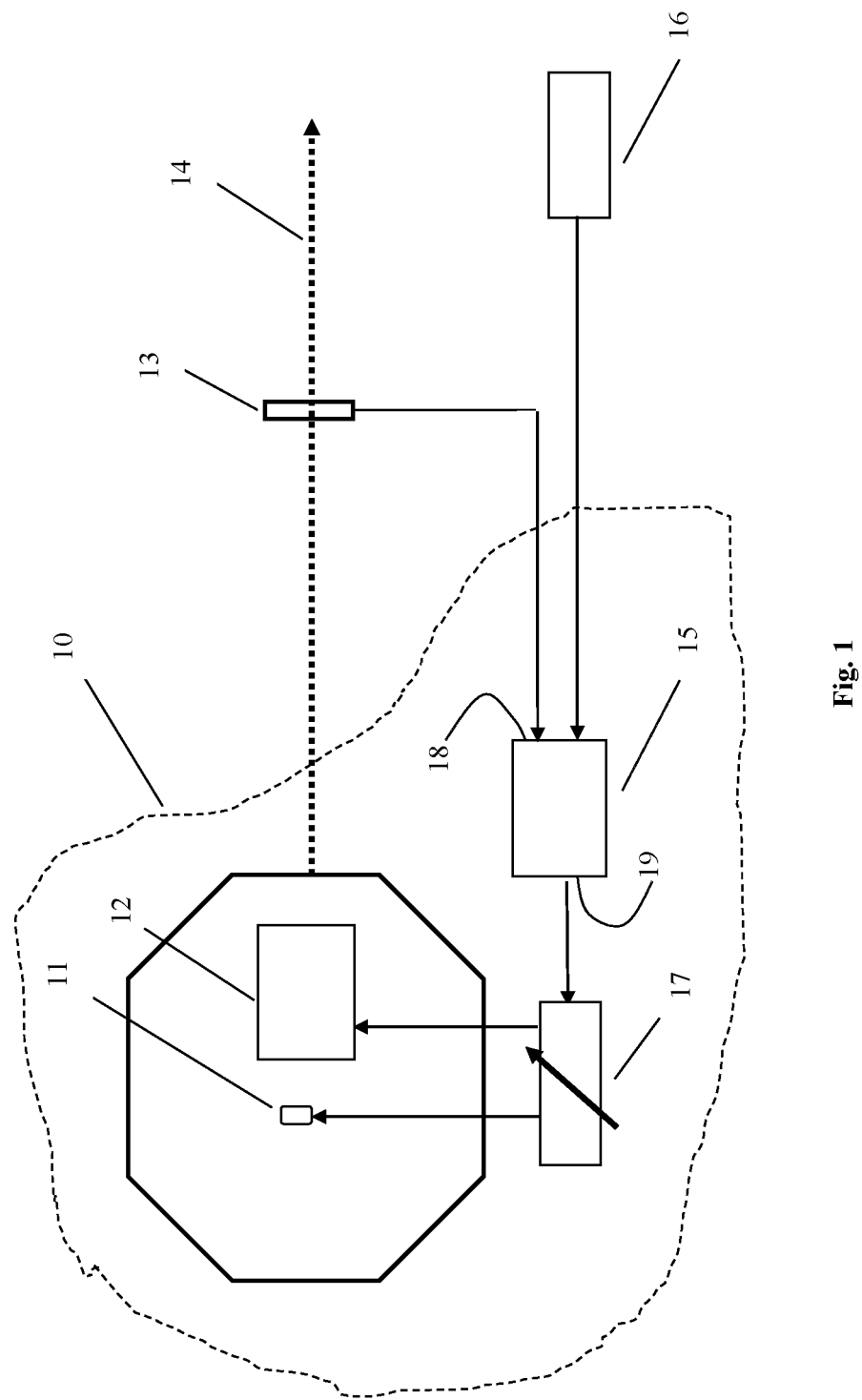
FIG. 1 shows a schematic representation of the device of invention and some additional elements.

FIG. 1 shows a schematic representation of a particle accelerator 10 and its controls according to the invention and some additional elements. The particle accelerator 10 (e.g. synchrocyclotron, linear accelerator, fixed field alternating gradient accelerator, . . . ) comprises an ion source 11, a radio frequency (RF) acceleration system 12 and means for varying 17 the number of particles within a beam pulse. Taking the example of a 250 MeV proton synchrocyclotron, typical RF acceleration frequencies are ranging between 50 and 100 MHz. In a synchrocyclotron, the RF acceleration system produces an RF wave with a time varying frequency whereby the frequency changes from high to low in order to take into account the mass increase of the particles during acceleration. For each beam pulse to be produced a total acceleration cycle is restarted whereby the frequency of the total acceleration cycle is determined by the RF modulation frequency (or RF repetition rate). Typical frequencies of RF repetition rate (or RF modulation frequency) are ranging between 200 Hz and 1000 Hz. A resulting beam pulse 14 is extracted from the accelerator at a frequency equal to the RF repetition rate. For example if the RF repetition rate is 500 Hz, the accelerator produces a beam pulse every 2 ms, the width of the beam pulse depends on the detailed design of the accelerator but is typically in the nanosecond to microsecond region. According to a preferred embodiment, the particle accelerator of the invention is configured to produce beam pulses whereof the beam pulse width is lower than 50 ms. For example the beam pulse width can be 0.5 microsecond.

Figure 2:
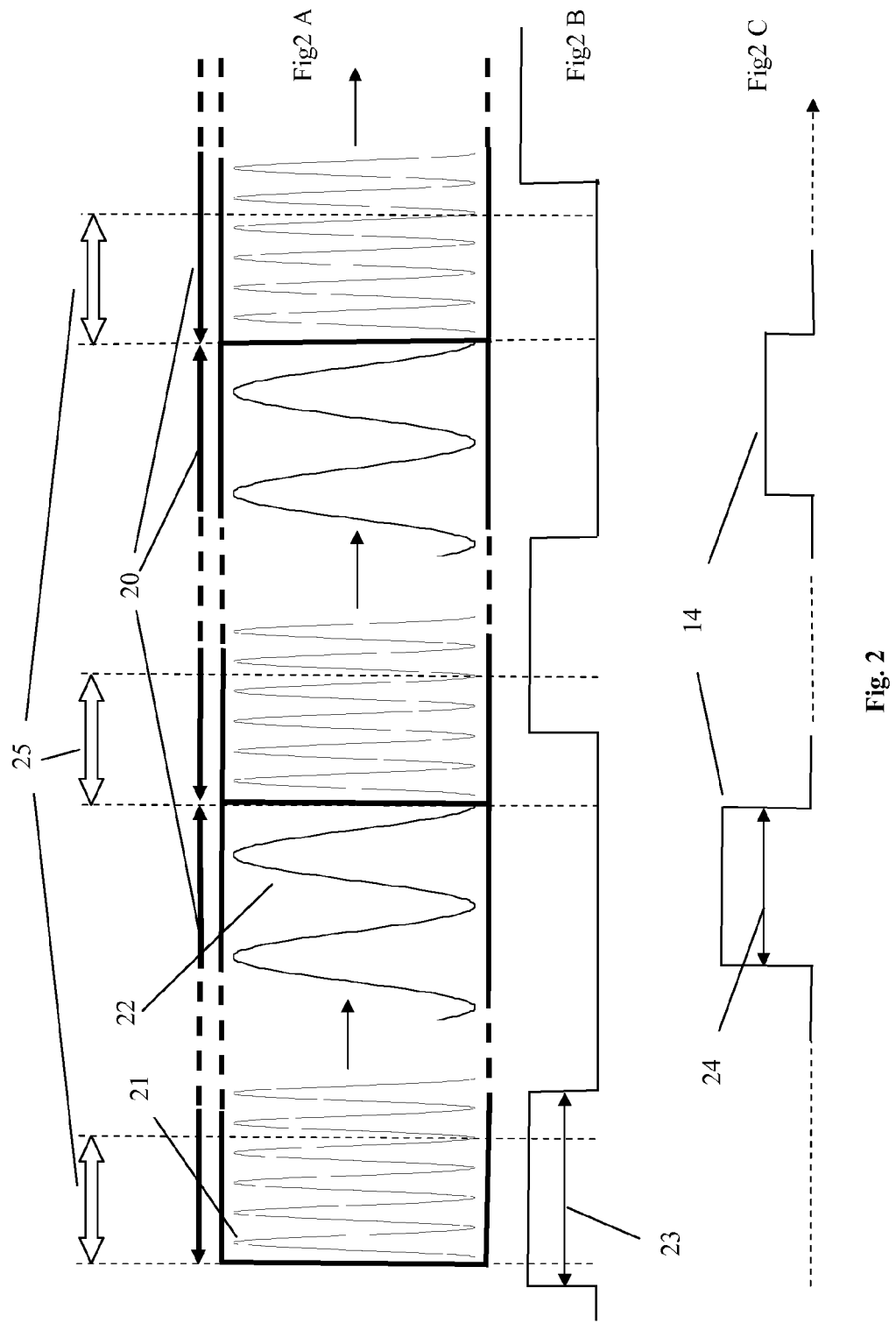
FIG. 2A shows a schematic representation of an example of a sequence of total acceleration cycles.
FIG. 2B shows the ion source on period in correlation with the sequence of total acceleration cycles of FIG. 2A.
FIG. 2C represents extracted beam pulses from a pulsed accelerator.

FIG. 2A shows a schematic representation of an example of a sequence of total acceleration cycles. The total acceleration cycle period 20 (also named RF repetition period) is schematically represented. For example in a synchrocyclotron this total acceleration cycle period 20 corresponds to the RF modulation period (e.g. 2 ms). FIG. 2 has not been made on a realistic scale and is basically a sketch to explain some elements of the invention. In practice, a particle in a synchrotron is making thousands of turns (e.g. 10000) before being extracted at the maximum energy and at each turn the particle gets accelerated through an electric field generated by the RF acceleration system. In FIG. 2A only a few (of the many thousand) single RF cycles of the RF wave generated by the RF accelerating system are shown as an illustration. As mentioned above, at the start of a new total acceleration cycle, the initial RF frequency (illustrated with initial RF cycles 21) of the RF wave is higher than the final RF frequency (illustrated with final RF cycles 22) in order to take into account the relativistic mass increase of the accelerated particles (for example 70 MHz as an initial value and 50 MHz as a final RF frequency value). As illustrated in FIG. 2C, for each total acceleration cycle 20, at a repetition defined by the frequency of RF modulation, a beam pulse 14 is extracted from the accelerator (e.g. every 2 ms). The beam pulse width 24 is for example 0.5 microseconds.

The accelerator 10 comprises means for varying the number of particles 17 within each beam pulse 14 from a minimum value (e.g. zero value) to a maximum value as function of the value of a beam control parameter. Various methods using various means and various beam control parameters can be employed to perform this intensity variation within a beam pulse. Four means for varying the number of particles 17 within a beam pulse and associated beam control parameters are discussed hereafter.

A first means for varying the number of particles within a beam pulse adjusts for each beam pulse a parameter controlling the amount of ions produced in the ion source 11. An ion source 11 typically comprises a cylindrical arc chamber or ion source body which is grounded and has a heated filament at one end and a floating anti-cathode at the other end. The filament or cathode is biased negatively with respect to the ground. The filament produces electrons. The electrons follow the magnetic field lines describing a very small helical path making the electron travel very long from one cathode to the other. A gas (typically a Hydrogen gas or another gas, depending on the particles desired for the particle beam) is injected in the interior of said ion source. The electrons lose part of their energy in the gas during their travel and create ionisation forming consequently a plasma column. Ion production in these type of ion sources can be varied by varying the ion source arc current. This may be achieved by changing the cathode voltage or by changing the heating current applied to the cathode filament. For other types of ion sources, a similar parameter can be selected as beam control parameter to vary the ion production of the ion source.

A second means to vary the number of particles within a beam pulse is to vary the acceleration voltage of the radio frequency acceleration system 12 as described in the above cited application WO2009056165. For example in a synchrocyclotron an alternating high voltage is applied to a Dee electrode. In this second method the amplitude of the alternating voltage of the Dee electrode is adjusted. Since the radius of curvature followed by a particle depends on the amount of energy gained by this particle, particles, having a difference in phase with respect to the alternating Dee voltage, gain different amounts of energy and have also, consequently, different orbit radius. Only particles falling within a given orbit range will be able to be efficiently be accelerated up to the maximum energy and be extracted from the synchrocyclotron. Hence by adjusting the acceleration voltage from beam pulse to beam pulse, the number of particles within a beam pulse can be varied on a pulse per pulse basis. In this second method, the beam control parameter is the acceleration voltage.

A third means to vary the number of particles within a beam pulse is to vary the time period during which the ion source 11 is turned on. In general, the ion source of a pulsed accelerator is operating in a pulsed mode and the ion source is only turned on for producing ions during a small fraction of the total acceleration period. By controlling the period the ion source 11 is turned on, the amount of ions extracted from the ion source can be varied and hence the number of particles accelerated within a total acceleration cycle period can be varied. In this third method the beam control parameter is the ion source on period.

A fourth means to vary the number of particles within a beam pulse is related to the synchronization of the operation of the ion source with respect to the operation of the RF acceleration system. In a pulsed accelerator, charged particles are extracted from the ion source and accelerated in discrete bunches to their final energy. For each such total acceleration cycle with a frequency defined by the RF repetition rate or the frequency of RF modulation (illustrated in FIG. 2A), a beam pulse 14 is extracted from the accelerator (illustrated in FIG. 2C). The total acceleration cycle 20 is illustrated on FIG. 2A together with the RF wave which has a time varying frequency, starting with a higher initial frequency 21 to a lower final frequency 22. In this fourth method, the ion source 'on' period 23 of the ion source 11 is kept constant for each total acceleration cycle. The parameter that is varied in this method is the time difference between the moment the ion source 11 is turned on and the moment the ions can start acceleration using the radio frequency acceleration system 12. For example in a synchrocyclotron, only during a small fraction of time, at the beginning of the total acceleration cycle 20, it is possible for ions to be captured in phase stable orbits and be accelerated up to their final energy. This small fraction of time can be called the acceptance period 25 where ions from the ion source can be accepted for acceleration. In FIG. 2A it is assumed that in a synchrocyclotron a number of "turns" are accepted by the acceleration system and the ion source is kept on during a few RF cycles. As illustrated in FIG. 2A and FIG. 2B, for the first total acceleration cycle 20 shown, the ion source is already turned on at the moment particles can start their acceleration (i.e. the ion source on period 23 starts before the begin of the acceptance period 25). When the ion source 11 was already turned on at the moment the ions can start acceleration and turned off at a moment where ions can not be accepted anymore for acceleration, the number of particles within a beam pulse 14 will be at maximum. However if the ion source is not on (i.e. not producing ions) at the time the total acceleration cycle is restarted and the ion source is only set on at a later moment, the number of ions in the beam pulse is reduced. This is illustrated in FIG. 2A and FIG. 2B where for the second total acceleration cycle 20, the ion source is turned on at a later moment, i.e. the ion source was still off during a part of the acceptance period 25. Depending on how much the ion source on period 23 is out of phase with respect to the acceptance period 25, the number of particles in the beam pulse can be reduced or even put to zero. For example for the third total acceleration cycle partly shown in FIG. 2A and FIG. 2B, the ion source is turned on too late, i.e. there is no overlap between the ion source on period 23 and the acceptance period 25 and hence in such a situation no beam pulse 14 is produced in this total acceleration cycle.

In FIG. 1 the means for varying the number of particles 17 is schematically represented. Depending on which of the four described methods is adopted the means for varying the number of particles 17 comprises the controls of the ion source 11 and/or controls of the RF acceleration system 12.

As shown on FIG. 1, the accelerator 10 comprises a beam control device 15 for controlling the beam pulse intensity. The beam control device 15 comprises fast digital logic circuits. For example a DSP (Digital signal processing) or FPGA (field-programmable gate array) based microprocessor can be used. This beam control device 15 is hereafter named a beam current control electronic unit (BCCEU).

The BCCEU 15 comprises a first interface 18 that interfaces with an external device 16 (e.g. control system) for receiving instructions. These instructions can be received in the form of a command value. This command value specifies then the required number of particles that need to be delivered within a beam pulse. For example, in the case of a spot scanning system, the dose to be delivered for each voxel is prescribed by the treatment planning system (not shown on FIG. 1). This dose which is generally expressed as a number of monitor units (or sometimes expressed as a dose in Gy) is translated into a quantity and in units that are compatible with the BCCEU. This quantity can for example be the number of particles (H+, C6+, . . . ) expressed as a number of particles or it can be an integrated charge expressed in Coulomb units.

Preferentially, the BCCEU comprises a memory where a calibration table is stored defining the relation between the value of a beam control parameter and the number of particles within a beam pulse. In an alternative embodiment, the relation between control parameter and number of particles can also be expressed by a mathematical function. If more than one beam control parameter is controlling the beam pulse intensity, multiple calibration tables or mathematical functions can be defined.

The BCCEU further comprises a second interface 19 for sending a command value or various commands values to the said means for varying the number of particles within a beam pulse. The command value specifies the value of the beam control parameter. As discussed above there are four methods and associated devices for varying the beam pulse intensity by varying specific beam control parameters. The command values will depend on the method implemented for varying the beam pulse intensity. For example if the third means for varying the number of particles is implemented the command value that can be sent is a command that specifies the ion source 'on' period.

The relationship between the control parameter and the beam pulse intensity can be experimentally defined by performing a calibration. Such a calibration requires the measurement of the number of particles within a beam pulse extracted from the accelerator. For this purpose a beam monitor 13 can be used to measure the number of particles (e.g. protons H+, carbon ions C6+, . . . ) within a beam pulse extracted from the accelerator 10. This monitor can for example be an ionization chamber. The exact position of the beam monitor does not play a role, this beam monitor can for example be installed at the exit of the accelerator or it can be installed more upstream from the accelerator or this monitor can be a beam monitor installed a beam delivery device (also called nozzle) within a treatment room. The nozzle is a component of a particle radiation therapy facility which is physically installed in the treatment room and is responsible for beam shaping and dosimetry.

The method of said calibration is now further discussed. The calibration data represent the number of particles within a single beam pulse extracted from the pulsed accelerator as a function of the setting value of a beam control parameter. The beam control parameter can be any control parameter with respect to the four methods described above for varying the beam pulse intensity. The data needed to generate a calibration curve is performed by repetitively producing and extracting beam pulses while for each beam pulse the value of the beam control parameter is gradually varied. The value of the beam control parameter is preferentially varied over the entire operating span of the beam control parameter. In summary, the recording of the calibration curve comprises the steps of:
1. setting first beam control parameter value (starting for example at the lowest operating value)
2. producing and extracting a beam pulse
3. measuring extracted beam pulse intensity
4. storing measured beam pulse intensity value
5. varying beam control parameter
6. repeating steps 2 to 5 for a series of beam control parameter values within a given operating span As a result a calibration data table is obtained comprising for a number of beam control parameter values, the corresponding number of particles within a beam pulse.

Alternatively, the data obtained through the calibration process can be fitted or approximated with a mathematical function. The parameters defining the mathematical function can be stored in a memory of the BCCEU.

In a preferred embodiment the entire process for generating the data needed to define a calibration curve is preferentially implemented as an automated computer controlled process. In this way, the calibration process can be repeated before each use of the accelerator. For example when the accelerator is used in a particle therapy radiation facility, the calibration can be performed before each patient irradiation.

When a calibration process has been completed, the delivery of a controlled pulsed beam can start. The BCCEU 15, through its first interface 18 with an external device 16 (e.g. control system), can receive instructions specifying the required number of particles that need to be delivered within a beam pulse. The required number of particles can be different from beam pulse to beam pulse. When the BCCEU receives an instruction to deliver a beam spot with a required number of particles the BCCEU will in a first step determine the required value for the beam control parameter. For this purpose the BCCEU can apply various means. One method is that the BCCEU is using the above discussed calibration data table. If the required number of particles is not equal to one of the calibration points, the BCCEU can perform an interpolation between the two data points that are the closest to the required data point. Alternatively, instead of using a calibration table with calibration points, the BCCEU can use a mathematical function as discussed above. In this case the required value of the beam control parameter can be directly calculated with the mathematical function. In a second step the BCCEU 15 will send the value of the required beam control parameter to the means to vary the number of particles 17, which will set the accelerator for producing a beam pulse having the required number of particles.

The beam pulses produced with the accelerator according to the invention can be delivered with high accuracy, i.e. the number of particles effectively delivered in a beam pulse (this is the beam pulse intensity) is equal the required number of particles within a certain tolerance. The fact that a high accuracy can be obtained for the beam pulse intensity with the described method is based on the observation that a series of physical quantities characterizing the performance of the accelerator remain unchanged or vary only slowly as function of time. These quantities are for example the ion source efficiency for producing ions, the acceleration efficiency of the ions and the efficiency for extracting the ions from the accelerator.

An alternative embodiment is now discussed which can further improve the accuracy of the beam pulse intensity. As there is a potential that the relation between the number of particles within a beam pulse and the value of a control parameter can slightly drift in time, it is proposed in an alternative embodiment to have a continuous update of the calibration data whenever the accelerator is producing beam pulses. For this purpose the BCCEU comprises control means to automatically readjust the calibration data after each produced beam pulse. This readjustment is made by comparing the measured number of particles received from a beam monitor with the required number of particles specified by an external system as discussed above. If the calibration data are stored in a calibration table as a list of control beam parameters with corresponding number of particles, there are various ways to update the list. For example if the comparison of the measured number of particles with the required number of particles is out of tolerance, a calibration data point can be added, a data point can be replaced with the new data point or existing data points can be readjusted. If the calibration data are approximated with a mathematical function a new fit to the updated calibration data and an update of the parameter values of the mathematical function can be made.

Figure 3:
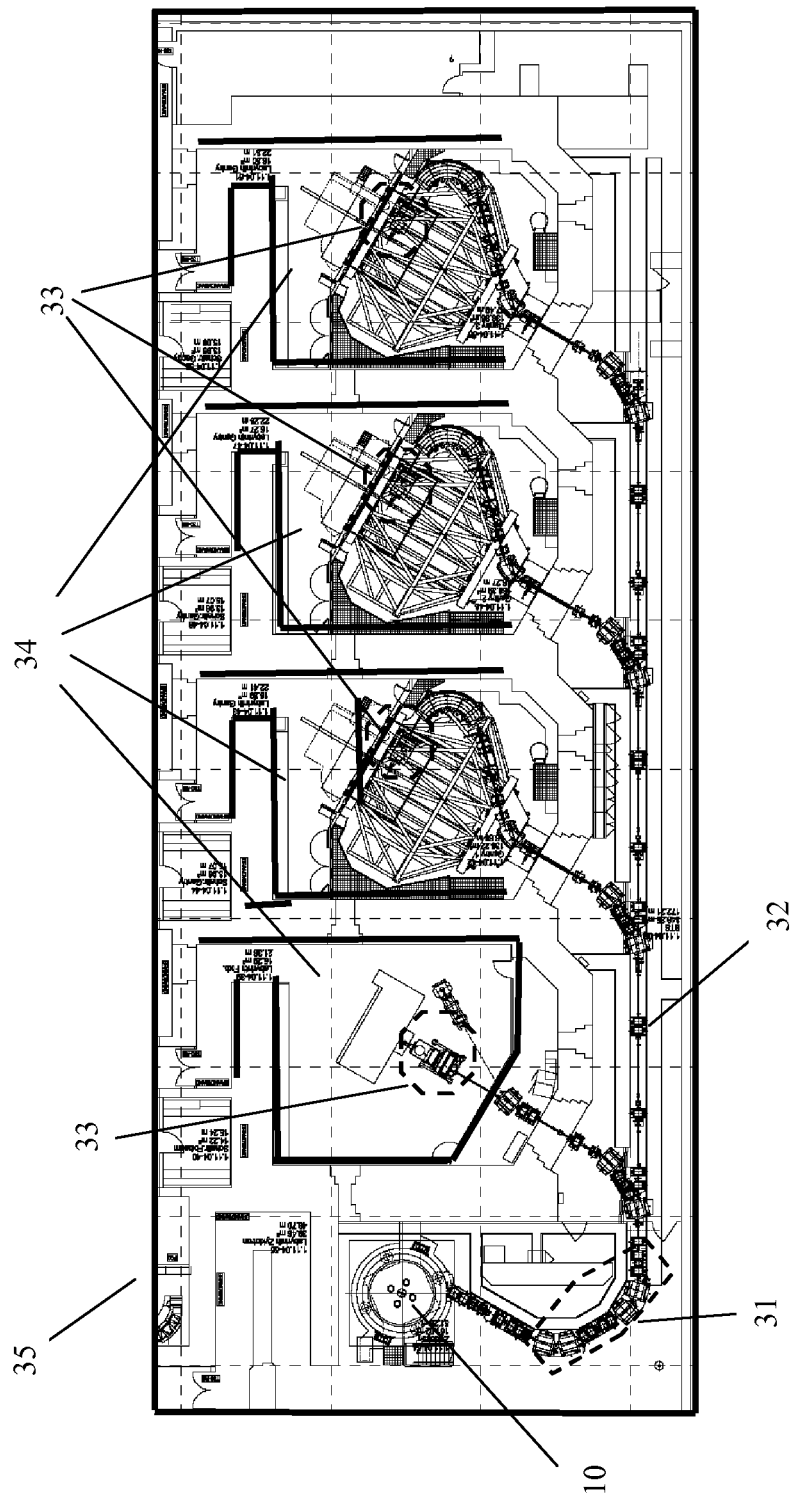
FIG. 3 shows an example of a layout of a particle radiation therapy facility comprising a particle radiation system according to the invention.

The accelerator 10 according to the invention is well suited for use in particle radiation therapy. FIG. 3 shows an example of a particle radiation therapy facility comprising a particle radiation therapy system 35 according to the invention. This particle radiotherapy system comprises besides the pulsed beam accelerator 10 (e.g. a synchrocyclotron) for producing energetic charged particles also means to vary the energy of the particle beam 31, a beam transport system 32 and a particle beam delivery device 33 (also called nozzle). The beam transport system is responsible to transport the beam to one or more treatment rooms 34. The particle beam delivery system 33 is responsible to deliver a conformal dose distribution to the target volume and monitor and measure the dose delivered. Various types of particle beam delivery systems exist, each applying different techniques to deliver a conformal dose to the target volume. There are two major techniques used in particle beam delivery: the more common passive scattering techniques and the more advanced scanning techniques.

An example of an advanced scanning beam delivery technique is the so called spot-scanning technique (Pedroni et al. in Med. Phys., 1995, 22 (1), 37-53). With the current invention, the problem of long irradiation times when using a pulsed accelerator for spot scanning can be solved. As discussed above, in spot scanning the target is typically divided in 5000 to 10000 voxels (i.e. elementary target volumes) and a prescribed dose needs to be delivered to each voxel with a precision of typically 1%. In spot scanning, dose is delivered to each voxel by performing a spot irradiation for each voxel. Moreover, Pedroni et al. proposed to perform multiple repainting of the target volume to compensate for organ motion and hence the total number of spot irradiations to complete a target irradiation is even more increased. In order to reduce the total target irradiation time to a reasonable value (typically 60 s) the irradiation time of a single spot irradiation needs to be reduced to the level of maximum a few milliseconds. If a pulsed beam from a synchrocyclotron is used and let say that the spot irradiation needs to be performed in 2 milliseconds in order to keep the irradiation time to a reasonable level, the spot irradiation will ideally need to be completed with a single beam pulse. As the beam pulse duration is extremely short as mentioned above, it is impossible to interrupt a beam pulse in the middle of the pulse and hence beam delivery can only be performed as an integer number of beam pulses. As a result, when a spot irradiation needs to be performed with only one or a limited integer number of beam pulses it is necessary to control the beam intensity of each individual beam pulse with high accuracy in order to be able to guarantee the required dose accuracy in the target volume.

With a pulsed beam accelerator according to the invention, spot scanning can be performed with the required accuracy of typically 1% and within a reasonable total irradiation time (a typical total irradiation time is 60 s). Indeed, as discussed above, by using means to vary the number of particles within a beam pulse by adjusting a beam control parameter and by generating calibration data defining the relation between the number of particles within a beam pulse and a beam control parameter it is possible to generate a single beam pulse containing a well defined number of particles and hence a single beam pulse can be used to perform a spot irradiation when using a spot scanning technique.

As discussed above, in an alternative embodiment of the invention, there is a continuous update of the calibration data whenever the accelerator is producing beam pulses. In addition to this feedback loop which permanently updates the calibration curve, two additional improved embodiments of using a pulsed beam accelerator for use with spot scanning are hereafter discussed.

In a first improved embodiment each spot irradiation is performed with two beam pulses instead of one beam pulse. The two beam pulses to deliver the total required number of particles for each spot irradiation are defined as follows:
1. the required number of particles for the first of said two beam pulses is defined as a given percentage (e.g. 90%) of the total required number of particles to be delivered for said spot irradiation.
2. the required number of particles for the second of said two beam pulses is defined as the total required number of particles for said spot irradiation minus the measured number of particles already delivered with said first beam pulse. For example if the required number of particles for the first beam pulse was set to 90% and the measured number of particles of this first beam pulse corresponds to 88%, the required number of particles for the second pulse will be set to 12%.

The measurement of the number of particles delivered during the first pulse is measured with a beam monitor. This beam monitor can be installed at the exit of the accelerator or somewhere along the beam transport system or preferentially it can be a beam monitor installed in the particle beam delivery device 33. The advantage of this two spot irradiation method is that the accuracy needed to produce the number of particles per pulse is reduced. Indeed even if a spot irradiation accuracy of 1% needs to be obtained a lower beam pulse intensity accuracy is acceptable. Suppose that, as an example, the beam pulse intensity accuracy that can be obtained with the accelerator is 5%. For the first beam pulse the required number of particles can be set to for example 90%. Taking into account a potential error of 5%, then the measured number of particles can for example be 86% (one would expect a number between 90+/−5%). With the method described above the second pulse is then set to 100%−86%=14% and the second pulse is then again delivered with an accuracy of 5%. In this example the total accuracy of the spot scanning irradiation would be 0.7% (0.05*14) and thus even with a pulse intensity accuracy of 5% a spot scanning irradiation can be performed with an accuracy of 1% or less.

In a second improved embodiment each spot irradiation is performed with a variable number of beam pulses. The idea is to deliver a large percentage of the total required number of particles with a variable number of pulses and then to use a last beam pulse to deliver the missing number of particles. The number of particles for each beam pulse are then defined as follows:

1. the first beam pulses of said variable number of beam pulses are defined such that the sum of the required number of particles is equal to a given percentage (e.g. 90%) of the total number of particles to be delivered for said spot irradiation. For example, if in total 4 pulses will be used to irradiate said spot, the first three beam pulses can be defined to deliver each 30% of the total number of particles to be delivered in the spot irradiation.
2. the required number of particles for the last beam pulse of said variable number of beam pulses is defined as the total number of particles to be delivered for the spot irradiation minus the measured number of particles already delivered for said spot irradiation. For example if in total 4 beam pulses will be used and the sum of the measured number of beam particles of the first three beam pulses corresponds to 87%, then the required number of particles for the last beam pulse is set to 13% of the total required number of particles.

This second improved embodiment can for example be used in combination with a spot scanning system where multiple repainting of the target volume are made. In such a system the dose to be delivered to one or more voxels can be divided in a number of "paintings". Suppose for example that a spot irradiation is divided in 10 paintings, the required number of particles for each of the first 9 paintings can be set to 10% of the total required number of particles. For the last painting, painting number 10, the required number of particles are determined in accordance with the measured number of particles delivered during the first 9 paintings.

The last embodiment can also be described as: a method for performing a spot irradiation by a number of beam pulses with a particle radiotherapy system comprising a particle accelerator according to the invention, i.e. an accelerator of the type synchrocyclotron or the like, provided with a means for receiving a specified number of particles for each beam pulse, and delivering said number of particles on the basis of pre-defined calibration tables or mathematical functions, the radiotherapy system further comprising a spot scanning beam delivery device configured to provide a series of spot irradiations. The method is thus characterized by the following steps, for each spot of said series of spot irradiations:

defining the total required number of particles T1 to be delivered to said spot,
specifying a total number of beam pulses for delivering said number of particles T1 and defining a required number of particles for each beam pulse of said total number of beam pulses,
applying said beam pulses, except the last beam pulse,
measuring the number of particles A1 of said beam pulses except the last beam pulse,
before applying the last beam pulse, calculating the difference T1−A1 between the total required number of particles and the measured number of particles,
specifying the required amount of particles in the last beam pulse A2 as equal to said difference T1−A1,
applying the last beam pulse The invention is thus also related to the use of a particle radiotherapy system comprising a particle accelerator according to the invention, i.e. an accelerator of the type synchrocyclotron or the like, provided with a means for receiving a specified number of particles for each beam pulse, and delivering said number of particles on the basis of pre-defined calibration tables or mathematical functions, the radiotherapy system further comprising a spot scanning beam delivery device configured to provide a series of spot irradiations, said use being characterized by the following steps, for each spot of said series of spot irradiations:

defining the total required number of particles T1 to be delivered to said spot,
specifying a total number of beam pulses for delivering said number of particles T1 and defining a required number of particles for each beam pulse of said total number of beam pulses,
applying said beam pulses, except the last beam pulse,
measuring the number of particles A1 of said beam pulses except the last beam pulse,
before applying the last beam pulse, calculating the difference T1−A1 between the total required number of particles and the measured number of particles,
specifying the required amount of particles in the last beam pulse A2 as equal to said difference T1−A1,
applying the last beam pulse According to the present invention, it is possible to control the number of particles within a beam pulse of a pulsed particle accelerator. The particle accelerator of the invention comprises means for varying the number of particles within each beam pulse based on parameter values of a beam control parameter and the accelerator comprises also calibration data defining the relation between the number of particles within a beam pulse and the said beam control parameter. This is of particular interest for performing so-called spot scanning irradiations in particle radiation therapy. A method is disclosed which allows spot scanning irradiations using a limited number of beam pulses and hence reducing the irradiation time and while at the same time obtaining a dose delivery with high accuracy.

In this description of the invention the term "number of particles" has been used to specify the quantity of particles within a beam pulse. The same term has been used to specify the information received from for example an external control system 16 or the information received from a beam monitor 13. Depending on the details of the specific realization of the device of invention, other quantities, other than "number of particles" can be used. For example if an ionization chamber is used as a beam monitor, what is measured is a dose and this is not a direct measurement of "number of particles". For a person skilled in the art, it is known how to relate the measured dose with the number of particles. The same holds for information received from a control system 16, also here the number of particles required in a beam pulse can be expressed using another quantity.

REFERENCE NUMBERS

10: Accelerator
11: Ion source
12: Radio frequency acceleration system

13: Beam monitor
14: Beam pulse
15: Beam Control Device
16: Control System
17: Means for varying number of particles
20: Total acceleration cycle period (=RF repetition period=RF modulation period)
21: Initial RF frequency
22: Final RF frequency
23: Ion source on period
24: Beam pulse width
31: Means for varying energy
32: Beam transport system
33: Beam delivery device
34: Treatment room
35: Particle radiotherapy system

The invention claimed is:

1. A particle accelerator of the type synchrocyclotron for producing an energetic pulsed ion beam, said accelerator comprising an ion source for producing ions and a radio frequency acceleration system for accelerating said ions, said accelerator comprising:
Means for varying the number of particles within each beam pulse of said pulsed ion beam from a minimum value to a maximum value as function of the value of a beam control parameter, said parameter being related to the operation of the ion source and/or of the RF system,
A beam control device comprising:
a first interface for receiving an external instruction specifying the required number of particles for each beam pulse;
a calibration table or parameter values of a mathematical function defining the relation between the value of said beam control parameter and said number of particles within a beam pulse, said table or parameters being stored on a suitable storing means;
means for determining the required value of said beam control parameter corresponding to said required number of particles using said calibration table or said mathematical function;
a second interface for sending said required value of said beam control parameter to said means for varying the number of particles;
the particle accelerator further compromising:
control means for automatically generating said calibration table or said mathematical function by defining a number of different values for said beam control parameter, producing for each said value a beam pulse and measuring the corresponding number of particles within each produced beam pulse.

2. The particle accelerator according to claim 1 wherein:
the first interface is configured for receiving an external signal specifying the measured number of particles within a beam pulse, said measurement being performed with a beam monitor; and
wherein the beam control device further comprises means for updating said calibration table or said parameter values in dependence of said measured number of particles.

3. The particle accelerator according to claim 2 further comprising:
control means for automatically readjusting said calibration table or said mathematical function after each beam pulse produced by said accelerator, said readjusting being made by comparing the said measured number of particles with the said required number of particles.

4. The particle accelerator according to claim 1, wherein said means for varying the number of particles within each beam pulse comprises means for varying the arc current of said ion source.

5. The particle accelerator according to claim 1, wherein said means for varying the number of particles within each beam pulse comprises means for varying the acceleration voltage of said radio frequency acceleration system.

6. The particle accelerator according to claim 1, wherein said means for varying the number of particles within each beam pulse comprises means for varying the time period during which the said ion source is turned on.

7. The particle accelerator according to claim 1, wherein said means for varying the number of particles within each beam pulse comprises means for varying the time difference between the moment the ion source is turned on and the moment the ions can start acceleration using said radio frequency acceleration system.

8. A particle radiotherapy system comprising a particle accelerator according claim 1.

9. The particle radiotherapy system according to claim 8 further comprising:
A spot scanning beam delivery device configured to provide a series of spot irradiations.

10. The particle radiotherapy system according to claim 9 whereby said spot scanning beam delivery device is configured to use a single beam pulse for each spot irradiation.

11. The particle radiotherapy system according to claim 9 wherein said spot scanning beam delivery device is configured to use two beam pulses to deliver the total required number of particles for each said spot irradiation, said particle radiotherapy device is further comprising:
Means to define the required number of particles for the first of said two beam pulses as being a given percentage of the total required number of particles to be delivered for said spot irradiation;
Means to specify the required number of particles of the second of said two beam pulses as being the said total required number of particles for said spot irradiation minus the measured number of particles already delivered with said first beam pulse.

12. The particle radiotherapy system according to claim 9 wherein said spot scanning beam delivery device is configured to use a variable number of beam pulses for each said spot irradiation, said particle radiotherapy device further comprising:
Means to define the required number of particles for all beam pulses of said variable number of beam pulses such that the sum of the required number of particles of all beam pulses except the last beam pulse equals a given percentage of the total number of particles to be delivered for said spot irradiation;
Means to specify the required number of particles for the last beam pulse of said variable number of beam pulses as being the total number of particles to be delivered for the said spot irradiation minus the measured number of particles already delivered for said spot irradiation.

13. A method for controlling the number of particles within a beam pulse from a pulsed beam particle beam accelerator, of the type synchrocyclotron, said beam pulses being usable for performing particle beam irradiations, said accelerator comprising means to vary the number of particles within each beam pulse as a function of the value of a beam control parameter, said beam control parameter being related to the operation of the ion source and/or the RF system, said method comprising the steps of:

Generating calibration data comprising the sub-steps of:
1. Applying a value of said beam control parameter to said means for varying the number of particles;
2. Producing and extracting a beam pulse from said accelerator;
3. Measuring number of particles within said extracted beam pulse;
3. Storing said measured number of particles within said extracted beam pulse; and
4. Repeating steps 1 to 4 for a series of beam control parameter values;

Performing particle beam production comprising the sub-steps of:
1. Receiving an external instruction specifying for each beam pulse the required number of particles within a beam pulse;
2. Determining the required value of said beam control parameter corresponding to said required number of particles using said calibration data;
3. Applying said required value of beam control parameter to said means for varying number of particles;
4. Producing and extracting beam pulse from said accelerator.

14. The method according to claim 13 wherein said step of performing particle beam production further comprises the sub-steps of:
5. Measuring the number of particles within said extracted beam pulse;
6. Making a comparison between said measured number of particles with said required number of particles;
7. Applying a correction to said calibration data based on said comparison.

15. A method for performing a series of spot irradiations by a number of beam pulses with the system of claim 9, wherein the method comprises for each spot of said series of spot irradiations the steps of:

defining the total required number of particles T1 to be delivered to said spot, specifying a total number of beam pulses for delivering said number of particles T1 and defining a required number of particles for each beam pulse of said total number of beam pulses, applying said beam pulses, except the last beam pulse, measuring the number of particles A1 of said beam pulses except the last beam pulse, before applying the last beam pulse, calculating the difference T1−A1 between the total required number of particles and the measured number of particles, specifying the required amount of particles in the last beam pulse A2 as equal to said difference T1−A1, applying the last beam pulse.

16. A particle accelerator of the type synchrocyclotron configured to produce an energetic pulsed ion beam, the accelerator comprising:

an ion source configured to produce a pulsed ion beam comprising ions;

a radio frequency acceleration system configured to accelerate the ions, wherein the number of particles within a beam pulse of the pulsed ion beam is varied from a minimum value to a maximum value as function of the value of a beam control parameter, the parameter being related to the operation of the ion source and/or of the RF system; and a beam control device comprising:
a first interface configured to receive an external instruction specifying the required number of particles for each beam pulse;
a memory configured to store a calibration table or parameter values of a mathematical function defining the relation between the value of the beam control parameter and the number of particles within a beam pulse; and
a second interface configured to send a required value of the beam control parameter corresponding to the required number of particles using the calibration table or the mathematical function; and
a controller configured to automatically generate the calibration table or the mathematical function by defining a number of different values for the beam control parameter, producing for each different value a beam pulse and measuring the corresponding number of particles within each produced beam pulse.

* * * * *